US008236926B2

(12) United States Patent
Thorson et al.

(10) Patent No.: US 8,236,926 B2
(45) Date of Patent: Aug. 7, 2012

(54) RAPID GLYCOPEPTIDE OPTIMIZATION VIA NEOGLYCOSYLATION

(75) Inventors: Jon S. Thorson, Middleton, WI (US); Byron R. Griffith, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 1264 days.

(21) Appl. No.: 11/850,877

(22) Filed: Sep. 6, 2007

(65) Prior Publication Data

US 2008/0114157 A1    May 15, 2008

Related U.S. Application Data

(60) Provisional application No. 60/824,660, filed on Sep. 6, 2006.

(51) Int. Cl.
*C07K 14/00* (2006.01)

(52) U.S. Cl. .................................. 530/345; 530/395

(58) Field of Classification Search ..................... None
See application file for complete search history.

(56) References Cited

OTHER PUBLICATIONS

Griffith et al., J. Am. Chem. Soc., Jul. 4, 2007, vol. 129, No. 26, pp. 8150-8155.*
Griffith et al., Current Opinion in Biotechnology, 2005, vol. 16, pp. 622-630.*
Murray, N. Engl. J. Med. 2000, 342, 710-721.
Kahne et al., Chem. Rev. 2005, 105, 425-448.
Weigel et al., Science 2003, 302, 1569-1571.
Chang et al., N. Engl. J. Med. 2003, 348, 1342-1347.
Nicolaou et al., Chem.-Eur. J. 2001, 7, 3798-3823.
Dong et al., J. Am. Chem. Soc. 2002, 124, 9064-9065.
Peri et al., Tetrahedron 1998, 54, 12269-12278.
Peri et al., Chem. Comm. 2002, 1504-1505.
Peri et al., Chem.-Eur. J. 2004, 10, 1433-1444.
Langenhan et al., Proc. Natl. Acad. Sci. U. S. A. 2005, 102, 12305-12310.
Thompson et al., J. Am. Chem. Soc. 1999, 121, 1237-1244.
Chen et al., Tetrahedron 2002, 58, 6585-6594.
Nagarajan et al., 1989, 42, 63-72.
Leimkuhler et al., J. Am. Chem. Soc. 2005, 127, 3250-3251.
Pitsch, Helv. Chim. Acta 1997, 80, 2286-2314.
Sleath et al., J. Org. Chem. 1991, 56, 3608-3613.
Hall et al., Carbohydr. Res. 1976, 47, 299-305.
Faghih et al., J. Org. Chem. 1986, 51, 4558-4564.
Guo et al., J. Am. Chem. Soc. 2002, 124, 10642-10643.
Williams et al., Tetrahedron 1967, 23, 1369-1378.
Zemplen, Ber. Deutsh. Chem. Ges. 1927, 60B, 1555.
Wang et al., J. Org. Chem. 1993, 58, 3985-3990.
Dahloff, Naturforsch. 1996, 51b, 891-896.
Tsuda et al., Chem. Pharm. Bull. 1991, 39, 2883-2887.
Maunier et al., Carbohydr. Res. 1997, 299, 49-57.
Durrwachter, Org. Chem. 1988, 53, 4175-4181.
Kadokawa, J. et al. Chem. Lett. 1998, 383-384.
Macher, Carbohydr. Res. 1987, 162, 79-84.
PCT/US2007/077712 International Search Report; Jul. 25, 2008.
B R Griffith et al., "Sweetening Natural Products via Glycograndomization," Current Opinion in Biotechnology, vol. 16, 2005, pp. 622-630.
B R Griffith et al., "Model for Antibiotic Optimization via Neoglycosylation: Synthesis of Lipoglyconeopeptides Active Against VRE," Journal of the American Chemical Society, vol. 129, No. 26, 2007, pp. 8150-8155.
Griffith, Byron R. et al. "'Sweetening' natural products via glycorandomization." Current Opinion in Biotechnology 16: 2005. pp. 622-630.

* cited by examiner

*Primary Examiner* — Christopher R. Tate
*Assistant Examiner* — Roy Teller
(74) *Attorney, Agent, or Firm* — Quarles & Brady LLP

(57) ABSTRACT

The present invention generally relates to methods and compositions for generating vancomycin analogs. Specifically the invention relates to generating a vancomycin library through chemoselective ligation of a sugar moiety with a vancomycin aglycon. In particular, the present invention provides a library of vancomycin analogs, where the member of the library comprises at least one vancomycin analog selected from 2'-N-acyldecanoyl-glucosyl vancomycin neoglycoside, 3'-N-acyldecanoyl-glucosyl vancomycin neoglycoside, 4'-N-acyldecanoyl-glucosyl vancomycin neoglycoside, 6'-N-acyldecanoyl-glucosyl vancomycin neoglycoside, 2'-N-acylbiphenyl-glucosyl vancomycin neoglycoside, 3'-N-acylbiphenyl-glucosyl vancomycin neoglycoside, 4'-N-acylbiphenyl-glucosyl vancomycin neoglycoside and 6'-N-acylbiphenyl-glucosyl vancomycin neoglycoside.

6 Claims, 6 Drawing Sheets

RAPID GLYCOPEPTIDE OPTIMIZATION VIA NEOGLYCOSYLATION

CROSS-REFERENCE TO RELATED APPLICATIONS

This application claims priority to U.S. Provisional Application No. 60/824,660, filed Sep. 6, 2006, which is hereby incorporated by reference herein.

STATEMENT RELATED TO FEDERAL FUNDING

This work was supported by the National Institutes of Health grants AI52218, CA84374, GM70637 and National Cancer Institute grant U19 CA113297. The federal government may have rights to this invention.

FIELD OF THE INVENTION

The present invention generally relates to methods and compositions for generating vancomycin analogs. Specifically the invention relates to generating a vancomycin library through chemoselective ligation of a sugar moiety with a vancomycin aglycon.

BACKGROUND OF THE INVENTION

Recent years have seen the global emergence of vancomycin-resistant enterococcus (VRE),[1,2] and this threat to human health was seriously increased by the recent transfer of vancomycin resistance to the more dangerous pathogen *S. aureus*.[3,4] The lack of alternative therapeutics for VRE has increased interest in developing new glycopeptide derivatives to circumvent vancomycin resistance.

Two viable approaches for optimizing known glycopeptide scaffolds have emerged—the chemical modification of existing scaffolds and/or sugar functional groups, and the chemoenzymatic diversification of sugar residues.[2,5] However, each approach suffers from distinct limitations that have limited the exploration of structure—activity relationships. For instance, to demonstrate the importance of glycolipid moieties in overcoming resistance, Kahne et al. have replaced the natural non-lipid containing disaccharide of vancomycin with the 2'-N-acyldecanoyl glucosyl moiety from teicoplanin to provide activity against VRE.[6] However, it remains unclear if the 2' position of glucose is optimal for lipid attachment in teicoplanin and whether lipids other than straight-chain variants would provide potent activity when attached to glucose in teicoplanin-like compounds because of the difficulties associated with synthesizing glycopeptide analogs with alternative lipid attachments.

Accordingly, the need exists for methods and techniques for creating a novel library of compounds that circumvents vancomycin resistance.

SUMMARY OF THE INVENTION

The present invention generally relates to methods and compositions for generating vancomycin analogs. Specifically the invention relates to generating a vancomycin library through chemoselective ligation of a sugar moiety with a vancomycin aglycon.

In one embodiment, the present invention provides a method of synthesizing a vancomycin analog from a parent vancomycin compound. This method comprises the steps of: (a) synthesizing an alkoxylamine-containing vancomycin aglycon from the parent vancomycin compound; (b) chemoselectively ligating a sugar moiety to the alkoxylamine-containing vancomycin aglycon of step (a) to result in the vancomycin analog; and (c) isolating the resulting vancomycin analog of step (b), wherein the resulting vancomycin analog is effective in inhibiting growth of Vancomycin Resistant Enterococci (VRE).

In an exemplary embodiment, the alkoxylamine-containing vancomycin aglycon is a methoxylamine-containing vancomycin analog. Other alkoxylamines include ethoxylamine, propyloxylamine and similar alkoxylamines known to one of ordinary skill in the art may also be used in this synthesis.

In another exemplary embodiment, the sugar moiety is selected from 2-N-acyldecanoyl-D-glucose, 3-N-acyldecanoyl-D-glucose, 4-N-acyldecanoyl-D-glucose, 6-N-acyldecanoyl-D-glucose, 2-N-acylbiphenoyl-D-glucose, 3-N-acylbiphenoyl-D-glucose, 4-N-acylbiphenoyl-D-glucose and 6-N-acylbiphenoyl-D-glucose. In this method, the resulting vancomycin analog is selected from 2'-N-acyldecanoyl-glucosyl vancomycin neoglycoside, 3'-N-acyldecanoyl-glucosyl vancomycin neoglycoside, 4'-N-acyldecanoyl-glucosyl vancomycin neoglycoside, 6'-N-acyldecanoyl-glucosyl vancomycin neoglycoside, 2'-N-acylbiphenyl-glucosyl vancomycin neoglycoside, 3'-N-acylbiphenoyl-glucosyl vancomycin neoglycoside, 4'-N-acylbiphenoyl-glucosyl vancomycin neoglycoside and 6'-N-acylbiphenoyl-glucosyl vancomycin neoglycoside. In this method, the sugar moiety stereoselectively ligates to the alkoxylamine-containing vancomycin aglycon in a β-position, resulting in a β-enantiomer vancomycin analog.

Another embodiment of the present invention provides a vancomycin analog selected from 2'-N-acyldecanoyl-glucosyl vancomycin neoglycoside, 3'-N-acyldecanoyl-glucosyl vancomycin neoglycoside, 4'-N-acyldecanoyl-glucosyl vancomycin neoglycoside, 6'-N-acyldecanoyl-glucosyl vancomycin neoglycoside, 2'-N-acylbiphenyl-glucosyl vancomycin neoglycoside, 3'-N-acylbiphenoyl-glucosyl vancomycin neoglycoside, 4'-N-acylbiphenoyl-glucosyl vancomycin neoglycoside and 6'-N-acylbiphenoyl-glucosyl vancomycin neoglycoside.

Other objects, features and advantages of the present invention will become apparent after review of the specification, claims and drawings.

DETAILED DESCRIPTION OF PREFERRED EMBODIMENTS

Figure 1:
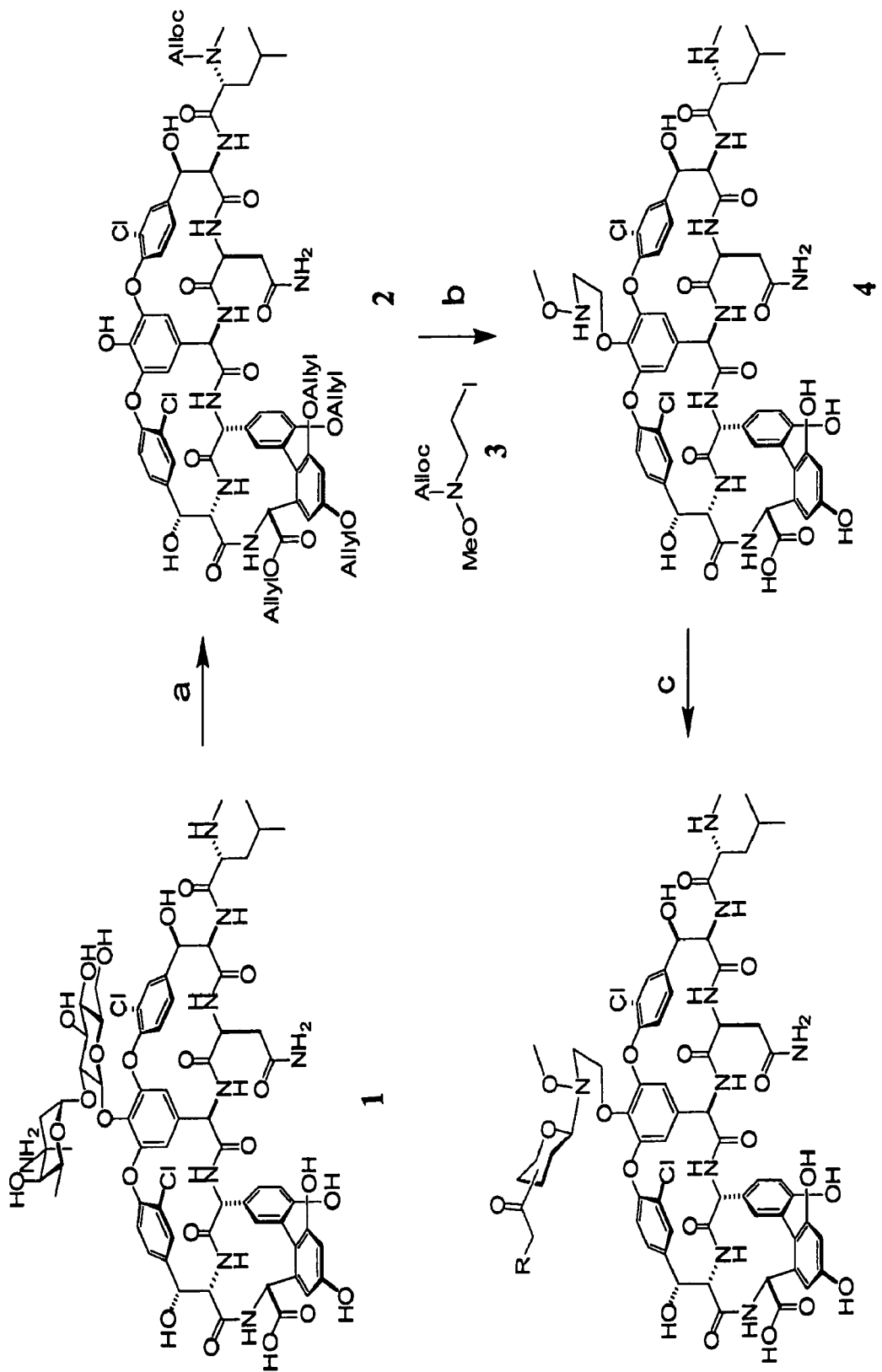
FIG. 1: Synthesis of neoglycoside lipoglycopeptide antibiotics. (a) (i) 4 equiv. of Alloc-OSu, 3.3 equiv. of $NaHCO_3$, DMF, rt, 16 h; (ii) 9 equiv. of allyl bromide, 4.5 equiv. of $Cs_2CO_3$, DMF, rt, 16 h; (iii) 1% HBr/HOAc, 6 equiv. of PhSH, rt, 0.5 h; (b) (i) 2 equiv. of (3), 1.2 equiv. of $Cs_2CO_3$, DMF, rt, 48 h; (ii) 0.7 equiv. of $Cl_2Pd(PPh_3)_2$, 120 equiv. of $Bu_3SnH$, DMF/HOAc (3:1), rt, 0.5 h, 49% crude (80% pure) over 5 steps; (c) 10 equiv. of N-acyl-D-glucose, 2.5% TFA/DMSO, 40° C., 24-72 h, 61% conversion (average).

This invention is not limited to the particular methodology, protocols, and reagents described, as these may vary. One of ordinary skill in the art may change the methodology, synthetic protocols and reagents as necessary. It is also understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

As used herein and in the appended claims, the singular forms "a", "an", and "the" include plural reference unless the context clearly dictates otherwise. Thus, for example, reference to "a sugar" includes a plurality of such sugars and equivalents thereof known to those skilled in the art, and so forth. Further, the terms "a" (or "an"), "one or more," "at least one," "comprising," "including," "characterized by" and "having" can be used interchangeably herein.

Any methods and materials similar or equivalent to those described herein can be used in the practice or testing of the present invention. All publications mentioned herein are incorporated herein by reference for the purpose of describing and disclosing the chemicals, cell lines, vectors, animals, instruments, statistical analysis and methodologies which are reported in the publications which might be used in connection with the invention. Nothing herein is to be construed as an admission that the invention is not entitled to antedate such disclosure by virtue of prior invention.

EXEMPLARY EMBODIMENTS OF THE PRESENT INVENTION

The present invention generally relates to methods and compositions for generating vancomycin analogs. Specifically the invention relates to generating a vancomycin library through chemoselective ligation of a sugar moiety with a vancomycin aglycon.

In one embodiment, the present invention provides a method of synthesizing a vancomycin analog from a parent vancomycin compound. This method comprises the steps of: (a) synthesizing an alkoxylamine-containing vancomycin aglycon from the parent vancomycin compound; (b) chemoselectively ligating a sugar moiety to the alkoxylamine containing vancomycin aglycon of step (a) to result in the vancomycin analog; and (c) isolating the resulting vancomycin analog of step (b). While some embodiments are directed to certain vancomycin compounds, this invention is equally applicable to other vancomycin compounds which have been synthesized via glycorandomization, a methodology that is well established in the art.

In this method, the resulting vancomycin analog is effective in inhibiting growth of Vancomycin Resistant Enterococci (VRE). In an exemplary embodiment, the alkoxylamine-containing vancomycin aglycon is a methoxylamine-containing vancomycin analog. Other alkoxylamines include ethoxylamine, propyloxylamine and similar alkoxylamines known to one of ordinary skill in the art may also be used in this synthesis.

In another exemplary embodiment, the sugar moiety is selected from 2-N-acyldecanoyl-D-glucose, 3-N-acyldecanoyl-D-glucose, 4-N-acyldecanoyl-D-glucose, 6-N-acyldecanoyl-D-glucose, 2-N-acylbiphenoyl-D-glucose, 3-N-acylbiphenoyl-D-glucose, 4-N-acylbiphenoyl-D-glucose and 6-N-acylbiphenoyl-D-glucose. Tthe resulting vancomycin analog is selected from 2'-N-acyldecanoyl-glucosyl vancomycin neoglycoside, 3'-N-acyldecanoyl-glucosyl vancomycin neoglycoside, 4'-N-acyldecanoyl-glucosyl vancomycin neoglycoside, 6'-N-acyldecanoyl-glucosyl vancomycin neoglycoside, 2'-N-acylbiphenyl-glucosyl vancomycin neoglycoside, 3'-N-acylbiphenoyl-glucosyl vancomycin neoglycoside, 4'-N-acylbiphenoyl-glucosyl vancomycin neoglycoside and 6'-N-acylbiphenoyl-glucosyl vancomycin neoglycoside. The sugar moiety stereoselectively ligates to the alkoxylamine-containing vancomycin aglycon in a β-position, resulting in a β-enantiomer vancomycin analog.

Another embodiment of the present invention provides a vancomycin analog selected from 2'-N-acyldecanoyl-glucosyl vancomycin neoglycoside, 3'-N-acyldecanoyl-glucosyl vancomycin neoglycoside, 4'-N-acyldecanoyl-glucosyl vancomycin neoglycoside, 6'-N-acyldecanoyl-glucosyl vancomycin neoglycoside, 2'-N-acylbiphenyl-glucosyl vancomycin neoglycoside, 3'-N-acylbiphenoyl-glucosyl vancomycin neoglycoside, 4'-N-acylbiphenoyl-glucosyl vancomycin neoglycoside and 6'-N-acylbiphenoyl-glucosyl vancomycin neoglycoside.

Provided below are examples of the present invention. These examples are provided for illustrative purposes only and should not be deemed to limit the scope of the invention.

In General

The present invention provides a strategy for glycopeptide optimization that involves chemoselective "neoglycosylation" chemistry and uses this methodology to rapidly optimize teicoplanin-vancomycin hybrid glycopeptide antibiotics by exploring both the nature of the lipid appendage and different sites of attachment for this critical substituent.

Neoglycosides are formed by chemoselective ligation of an unprotected, unactivated reducing sugar with an alkoxyamine-containing aglycon.[7] Stereoselectivity depends on the sugar donor, and in the case of glucose and GlcNAc, the β-anomer forms exlusively.[7-9] Neoglycosylation allows for the rapid construction of biologically active glycosides that are prohibitively difficult to synthesize by traditional chemical glycosylation.[10] When applied to glycopeptide optimization, neoglycosylation provides insights into structure-activity relationships that have not been explored.

The requisite methoxylamine functionality was installed at the A4 position of vancomycin, which is the natural position of disaccharide attachment (FIG. 1). Specifically, the Alloc/Allyl-protected vancomycin aglycon (2) was prepared according to a modified literature procedure.[11] To highlight the ease and scalability of the installation of the reactive alkoxyamine functional group, this route was carried out on multi-gram scale, starting with 16 g of vancomycin (1). Alloc-protected methoxylamine (3) was installed on the aglycon selectively at the A4 position, and global deprotection by Pd-catalyzed deallylation smoothly provided the methoxyamine-containing vancomycin aglycon (4). Throughout this route, crude products were submitted to the next step without further purification, and due to the chemoselectivity of neoglycosylation, the crude nature of aglycon (4) had no ill effect on the key glycosylation reaction.

Crude aglycon (4) was stirred with a 10-fold excess of 2'-N-acyldecanoyl-D-glucose in 2.5% TFA/DMSO, and the ligation reaction was monitored by HPLC. After 48 h, the reaction reached completion, and the newly generated material was isolated. NMR and FT-MALDI-MS analyses were consistent with the expected product (5) and revealed a β-configured glucosidic linkage (J=9.6 Hz).

Preliminary testing of neoglycoside (5) against VRE revealed significant activity showing that the use of an unnatural sugar linkage is compatible with overcoming vancomycin resistance.[12] The efficiency of neoglycosylation allowed the quick prepararation of eight analogs in which each position of glucose was substituted with either a straight-chain or biphenyl lipid appendage through an amide bond (FIG. 2a).

Using 50 mg of crude aglycon (4) per reaction, seven additional compounds (FIG. 2a) were synthesized in parallel according to the procedure described above. The glucolipid donors were prepared directly from the corresponding aminoglucosides, which were either commercially available or prepared according to literature procedures.

In the final neoglycosylation reaction, all eight sugar donors employed reacted efficiently to provide the desired products in a single step and with complete β stereoselectivity. These results represent the first successful use of glycolipids in methoxyamine-based neoglycosylation and highlight the generality of this approach.

Liponeoglycopeptides and aglycon (4), in purified form, were tested against a panel of fifteen different (1)-resistant clinical isolates of Enterococci, representing low- and high-level VRE. FIG. 2b illustrates the corresponding VRE activity of these liponeoglycopeptides, with the best compound displaying a >40-fold enhancement in potency over (1). This broad analysis revealed the N'-biphenyl analogues display specificity toward the low-level VRE strains and the N'-decanoyl derivatives display specificity toward the highly resistant strains.

Interestingly, while the N'-decanoyl series performed better overall, both compounds showed a marked preference for substitution at the sugar 3'- or 4'-position. Therefore, in this series of compounds, antibiotic activity was optimized by accessing chemical diversity previously unknown in this class of compounds. Additionally, these results suggest that the natural 2'-N-acyldecanoyl-glucosyl moiety found in teicoplanin is not, in fact, the optimal arrangement for activity against VRE.

The present invention provides a purely chemical method for the rapid optimization of the glycolipid portion of lipoglycopeptide antibiotics that is simple to perform on large scale, requires minimal synthetic effort in sugar donor preparation, and provides access to highly active antibiotics that are not easily prepared by other state-of-the-art methods. The results demonstrate that the natural O-glycosidic linkage can be replaced with the neoglycoside N-glycosidic linkage while enhancing biological activity. Further, attaching the lipid at the unnatural 3'- or 4'-position of glucose is shown to provide better activity than substituting the same moiety at the natural 2'-position. In light of recent findings that lipoglycopeptide antibiotics inhibit the transglycosylase step of bacterial wall biosynthesis, these optimized compounds may prove invaluable in more precisely elucidating the mechanism by which liponeoglycopeptides inhibit transglycosylastion.[14]

Materials and Methods

All moisture sensitive reactions were performed in flame-dried glassware under an atmosphere of Argon (Ar). Reaction temperatures were recorded as external bath temperatures. The phrase "concentrated under reduced pressure" refers to the removal of volatile materials by distillation using a Büchi rotary evaporator at water aspirator pressure (<20 torr) followed by removal of residual volatile materials under high vacuum. The term "high vacuum" refers to vacuum achieved by a standard belt-drive oil pump (<1 torr). Analytical thin layer chromatography (TLC) was performed on E. Merck TLC plates pre-coated with silica gel 60 $F_{254}$ (250 μm thickness). Visualization was accomplished using short wavelength UV light or potassium permanganate stain. Flash column chromatography (FCC) was performed on Silicycle silica gel (40-60 μm, 60 Å pore size). Water was MQ grade. All reagents were purchased from Aldrich (Milwaukee, Wis.), Sigma (St. Louis, Mo.), or Fisher Scientific (Pittsburgh, Pa.) and used without further purification.

HPLC was performed on a Gilson instrument equipped with a Gilson 321 pump, a Gilson 170 diode array detector, a Gilson 235 autoinjector, a Gilson 204 fraction collector, and UniPoint 3.2 software. Proton nuclear magnetic resonance ($^1$H NMR) and carbon NMR ($^{13}$C NMR) spectra were recorded on Varian UNITYINOVA 400 MHz, 500 MHz, and 800 MHz spectrometers in deuterated sovents. Chemical shifts are reported in parts per million (ppm, δ) relative to residual solvent peaks ($CHCl_3$: $^1$H: δ 7.26, $^{13}$C: δ 77.0; MeOH: $^1$H: δ 3.31, $^{13}$C: δ 49.2; $H_2O$: $^1$H: δ 4.78; DMSO: $^1$H: δ 2.49, $^{13}$C: δ 39.5). $^1$H NMR peak multiplicity with observed first order coupling is designated as singlet (s), doublet (d), triplet (t), quartet (q), and pentet (p). Peak multiplicity with observed non-first order coupling is designated as multiplet (m), and broad (br). Electron ionization mass spectra (ESI-MS) were obtained on an Agilent 1100 HPLC-MSD SL quadrupole mass spectrometer equipped with both orthogonal pneumatically assisted electrospray and atmospheric pressure chemical ionization soiurces. MALDI mass spectra (FT-MALDI-MS) were obtained using an IonSpec HiResMALDI FT-Mass spectrometer.

Synthesis Of Neoglycosylation Aglycon (4)

N,N'-Dialloc-tri-O-allyl vancomycin aglycon allylester (2). Referring again to FIG. 1, this intermediate was synthesized according to a modification of literature procedure.[15] The amines were protected according to the referenced protocol starting with 16 g of vancomycin.HCl, and 17 g of crude product were obtained. This crude material (17 g, 11 mmol) was dissolved in DMF (110 L), and finely powdered $Cs_2CO_3$ (16 g, 50 mmol) was added, and the mixture was stirred vigorously under Ar at room temperature (rt). Allyl bromide (8.4 mL, 12 g, 99 mmol) was added dropwise over 15 min, and the reaction was stirred overnight at rt. After 16 h, the mixture was precipitated into $H_2O$ (1.3 L), and the product was isolated by centrifugation at 3000×g for 30 min. at rt. The resulting pellets were dissolved in MeOH, combined in a separate flask, and the MeOH was removed under reduced pressure to yield an off-white solid (19 g, 97% yield over two steps). This crude material was subjected to the next reaction without further purification.

Thiophenol (6.2 mL, 6.7 g, 60 mmol) was added to a solution of compound (2) (18 g) dissolved in HOAc (310 mL) and stirred at rt. Hydrolysis was initiated by the addition of 3% HBr/HOAc (150 mL) and allowed to continue for 30 min. The solution (500 mL) was divided into 2 250 mL portions which were each precipitated into 10% brine (3.6 L). Precipitation into pure $H_2O$ resulted in the formation of a white hazy solution, suggesting less than complete precipitation. A 10% brine was effective in salting out this suspension and produced a white flocculent solid that was easily isolated by centrifugation at 3000×g for 10 min at rt. The combined pellets were washed with five portions of H$_2$O (100 mL) and stored under high vacuum overnight to yield an off-white solid. This material was filtered through a plug of silica gel by the elution of residual thiophenol with 1% MeOH in CH$_2$Cl$_2$ (500 mL). The crude product was eluted with 25% MeOH in CH$_2$Cl$_2$ (3 L), and solvent was removed under reduced pressure to yield on off-white solid (11 g, 78% yield). FT-MALDI MS m/z calculated for C$_{69}$H$_{72}$Cl$_2$N$_8$O$_{19}$[M+Na$^+$] 1409.4, observed 1409.4.

Neoglycosylation aglycon (4). Finely ground Cs$_2$CO$_3$ (3.7 g, 11 mmol) and compound (3) (4.6 g, 16 mmol) were added to a solution of compound (2) (11 g, 7.9 mmol) dissolved in DMF (37 mL) and stirred under Ar at rt. After 48 h, the mixture was neutralized by adding HOAc until the solution clarified. Volatiles were removed under high vacuum, and the residue was filtered through a plug of silica gel using 1% MeOH in CH$_2$Cl$_2$ (500 mL) to recover unreacted compound (3) and 25% MeOH in CH$_2$Cl$_2$ (1 L) to elute the crude product. Solvent was removed under reduced pressure to provide an off-white foam (11 g, 90% yield). FT-MALDI MS m/z calculated for C$_{76}$H$_{83}$Cl$_2$N$_9$O$_{22}$ [M+K$^+$] 1582.5, observed 1582.5.

Unreacted compound (3) was recovered by removal of solvent from the initial eluent under reduced pressure to provide a pale yellow oil (0.96 g) that was identical to authentic compound (3) in all respects.

Global deprotection of the crude material from the previous step was performed under conditions similar to those reported for the deprotection of a similar vancomycin synthetic intermediate.[15] Palladium dichloride-bis-triphenylphosphine (0.32 g, 0.46 mmol) was dissolved in warm DMF (60 mL) under Ar, and the solution was allowed to cool to rt. The crude material from the previous step (1.0 g, 0.65 mmol) was added and allowed to dissolve completely. To the solution was added HOAc (20 mL), and Bu$_3$SnH (1.7 mL, 1.9 g, 6.5 mmol) was added immediately under vigorous stirring. After 5 min., another portion of Bu$_3$SnH was added and the same amount was added every 5 min. until a total of twelve such portions had been added.

While adding BU$_3$SnH, the solution color gradually changed from yellow to golden brown to very dark brown after eight portions. An additional four portions were added to ensure complete consumption of the starting material. The final solution was stirred for 3.5 h at rt. The crude product was isolated by precipitation into acetone (500 mL) followed by centrifugation at 3000×g for 5 min. at rt. The combined pellets were dissolved in 95% MeOH/H$_2$O (120 mL), and H$_2$O (480 mL) was slowly added under vigorous stirring over 15 min.

Figure 3:
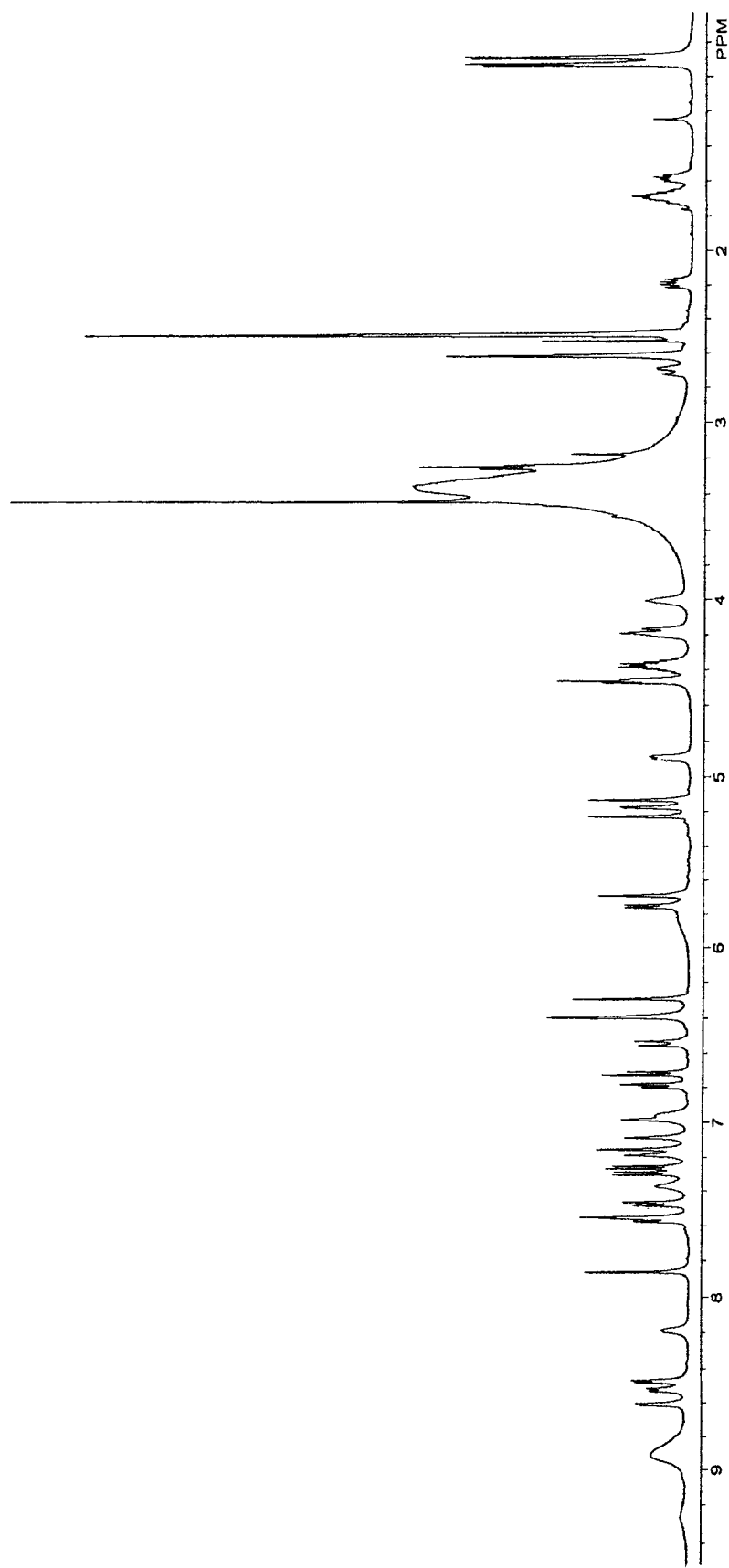
FIG. 3: ¹H NMR of compound (4).

The supernatant was isolated by centrifugation as before, and the concentration of product was quantified by HPLC analysis (Phenomenex LUNA C18 (2) column (4.6×250 mm, 5 µm particle size), eluting with a 25 min linear gradient from 5% CH$_3$CN in 0.1% TFA/H$_2$O to 30% CH$_3$CN in 0.1% TFA/H$_2$O, flow rate of 1 mL/min, and UV detection at 285 nm) and comparison to a standard curve constructed with HPLC-purified product (Discovery BIO Wide Pore C18 column (21.2× 250 mm, 10 µm particle size), eluting with a 25 min linear gradient from 5% CH$_3$CN in 0.1% TFA/H$_2$O to 30% CH$_3$CN in 0.1% TFA/H$_2$O, flow rate of 10 mL/min, and UV detection at 285 nm). This analysis showed the presence of 0.43 g of product. The solvent was removed under reduced pressure and the remaining residue was lyophilized overnight to provide the crude compound (4) as an off-white solid (0.55 g, 70% crude yield). The crude product was, therefore, 78% pure. FT-MALDI MS m/z calculated for C$_{56}$H$_{59}$Cl$_2$N$_9$O$_{18}$ [M+H$^+$] 1216.3, observed 1216.3. The $^1$H NMR spectrum at 60° C. and 500 MHz is shown in FIG. 3.

Alloc-protected methoxylamine. Methoxylamine.HCl (5.0 g, 60 mmol) was added to H$_2$O (50 mL) at 0° C. After 5 min., NaHCO$_3$ (11 g, 130 mmol) was added, and after 10 min, THF (100 mL) was added, and the solution was stirred at 0° C. for 5 min. Alloc-Cl (4.9 mL, 5.6 g, 46 mmol) was added dropwise over 10 min., and the solution was allowed to warm to rt after stirring an additional 15 min at 0° C. After 3.5 h, the layers were separated, and the aqueous layer was extracted with two portions of Et$_2$O (50 mL). The combined organic layers were diluted with Et$_2$O (250 mL) and washed with H$_2$O (50 mL), 1 N HCl (50 mL) and H$_2$O (50 mL). This layer was dried over Na$_2$SO$_4$, and solvent was removed under reduced pressure to provide a colorless oil (5.7 g, 94% yield) that required no further purification. $^1$H NMR (CDCl$_3$, 400 MHz) δ 8.33 (s, 1H), 5.78 (m, 1H), 5.19 (dm, 1H), 5.09 (dm, 1H), 4.50 (dm, 2H), 3.58 (s, 3H); $^{13}$C NMR (CDCl$_3$, 100 MHz) δ 157.1, 131.7, 117.9, 65.7, 64.0; ESI-MS m/z calculated for C$_5$H$_9$NO$_3$ [M+H$^+$] 132.0, observed 132.0. HRMS: m/z calculated for C$_5$H$_9$NO$_3$ [M+Na]$^+$ 154.0480, observed 154.0478.

N-Bromoethyl-Alloc-protected methoxylamine. NaH (95%, 0.45 g, 18 mmol) was added to a solution of compound (15) (2.4 g, 18 mmol) in DMF (23 mL) in two portions at 0° C. under Ar. After H$_2$ evolution ceased, the solution was allowed to warm to rt with stirring. Dibromoethane (2.3 mL, 5.0 g, 18 mmol) was added dropwise over 15 min., and the solution was stirred at rt overnight. After 16 h, the volatiles were removed under high vacuum, and the residue was dissolved in CH$_2$Cl$_2$ (50 mL). This solution was washed with two portions of H$_2$O (25 mL) and brine (25 mL), dried over Na$_2$SO$_4$, and the solvent was removed under reduced pressure. The oily residue was purified by FCC (10% EtOAc in Hexanes) to provide a very pale yellow oil (5.0 g, 71% yield). $^1$H NMR (CDCl$_3$, 400 MHz) δ 5.90 (m, 1H), 5.30 (dm, 1H), 5.20 (dm, 1H), 4.61 (dm, 2H), 3.83 (t, 2H), 3.70 (s, 3H), 3.46 (t, 2H); $^{13}$C NMR (CDCl$_3$, 100 MHz) δ 156.3, 131.9, 118.2, 66.6, 62.7, 50.6, 27.2; ESI-MS m/z calculated for C$_7$H$_{12}$BrNO$_3$ [M+H$^+$] 238.0, observed 238.0

N-Iodoethyl-Alloc-protected methoxylamine. NaI (5.0 g, 33 mmol) was added to a solution of compound (16) (6.0 g, 25 mmol) in acetone (65 mL), and the solution was refluxed overnight. After 16 h, the solvent was removed under reduced pressure to yield a pale yellow oil. The oil was dissolved in CH$_2$Cl$_2$ (50 mL) and washed with two portions of H$_2$O (25 mL) and brine (25 mL), dried over Na$_2$SO$_4$, and the solvent was removed under reduced pressure to provide a pale yellow oil (5.3 g, 74% yield) that required no further purification. $^1$H NMR (CDCl$_3$, 400 MHz) δ 5.90 (m, 1H), 5.30 (m, 1H), 5.21 (m, 1H), 4.62 (m, 2H), 3.80 (t, 2H), 3.70 (s, 3H), 3.24 (t, 2H); $^{13}$C NMR (CDCl$_3$, 100 MHz) δ 156.0, 131.9, 118.2, 66.6, 62.8, 51.5, −0.51; ESI-MS m/z calculated for C$_7$H$_{12}$INO$_3$ [M+H$^+$] 286.0, observed 286.0. HRMS: m/z calculated for C$_7$H$_{12}$INO$_3$ [M+Na]$^+$ 307.9760, observed 307.9760.

Synthesis of the Lipoglycopeptide Library

Figure 2:
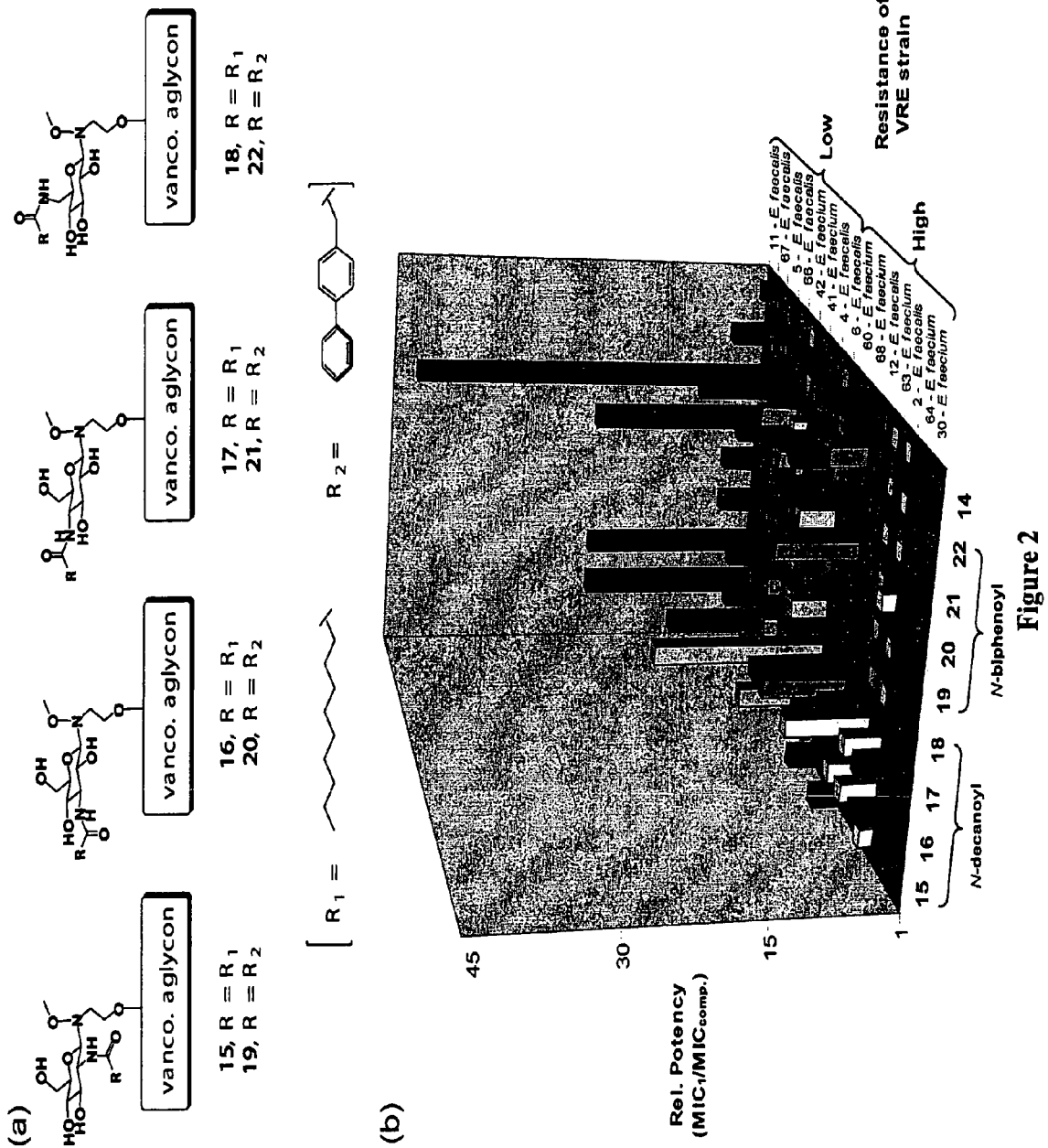
FIG. 2: Structure and activity of neolipoglycopeptides. (a) substitutions at position A4; (b) relative potency of neolipoglycopeptides against a VRE panel as defined by the MIC of (1) ($MIC_1$) divided by the MIC of the compound of interest ($MIC_{comp.}$) for each strain. MIC values were obtained using a standard microdilution assay. The MIC is defined as the lowest concentration at which no growth was visible after incubation at 35° C. for 22 h. VRE strains showed $MIC_1$ from 1 to 1024 ug/ml and included primary clinical isolates ad standard ATCC strains. An asterisk (*) indicates no bacteriostatic activity was observed at or below the compound's solubility limit (100 ug/ml) under assay conditions.

Referring now to FIG. 2, the lipoglycopeptide library is described.

2'-N-acyldecanoyl-glucosyl vancomycin neoglycoside (15). Aglycon (4) (60 mg crude, 50 mg aglycon, 0.041 mmol, 42 mM) was added to a solution of 2-N-acyldecanoyl-D-glucose (0.14 g, 0.41 mmol) in DMSO (0.97 mL) at 40° C. and stirred until completely clear. The glycosylation was initiated by adding TFA (24 µL), and the solution was stirred at 40° C. After 24 and 48 h, an aliquot (4 µL) of the reaction was diluted into 1:1 MeOH/H$_2$O (100 µL), and a white precipitate was observed. The suspension was sonicated for 1 min., centrifuged at 18 000×g for 1 min. at rt, and the supernatant (50 μL) was analyzed by HPLC (Phenomenex LUNA C18 (2) column (4.6×250 mm, 5 μm particle size), eluting with a 45 min linear gradient from 5% $CH_3CN$ in 0.1% $TFA/H_2O$ to 50% $CH_3CN$ in 0.1% $TFA/H_2O$, flow rate of 1 mL/min, and UV detection at 285 nm).

After 48 h, the reaction solution was purified on LH-20 using DMSO as eluent. TLC analysis of column fractions indicated complete separation of product and excess 2-N-acyldecanoyl-D-glucose. Both materials were recovered separately by combining relevant fractions and removing solvent under high vacuum. The product-containing material was purified via HPLC (Discovery BIO Wide Pore C18 column (21.2×250 mm, 10 μm particle size), eluting with a 20 min linear gradient from 20% $CH_3CN$ in 0.1% $TFA/H_2O$ to 45% $CH_3CN$ in 0.1% $TFA/H_2O$, flow rate of 10 mL/min, and UV detection at 285 nm) and collected in tubes containing 0.1 M $NH_4OAc$ (0.3 mL) to neutralize TFA.

Relevant fractions were combined, $CH_3CN$ was removed under reduced pressure, and $H_2O$ was removed by lyophilization to provide a white solid. This material was dissolved in 5% $MeOH/H_2O$ (48 mL) and desalted by solid phase extraction using a Waters Oasis® HLB cartridge (0.5 g) according to the manufacturers recommended protocol. The $CH_3CN$ was removed from relevant fractions under reduced pressure, and $H_2O$ was removed by lyophilization to provide a white flocculent solid (16 mg, 25%). The diagnostic glucose H-1 $^1H$ signal was identified by characterizing the product by TOCSY, gHSQC, and gHMBC NMR experiments at 60° C. with a 500 MHz spectrometer. The value of $J_{1,2}$ was obtained from a 1D TOCSY experiment at 45° C. with an 800 MHz spectrometer. Diagnostic $^1H$ NMR peak (800 MHz, DMSO-$d_6$, 318 K): δ 4.17 (d, $J_{1,2}$=9.6 Hz, glucose H-1). The regioselectivity of glycosylation was verified through observing a correlation between the glucose H-1 proton and the carbon of the methylene adjacent to the glycosidic nitrogen in an HMBC experiment. FT-MALDI-MS m/z calculated for $C_{72}H_{88}Cl_2N_{10}O_{23}$ [M+Na]$^+$ 1553.5, observed 1553.5.

3'-N-acyldecanoyl-glucosyl vancomycin neoglycoside (16). The product was prepared according to the procedure described above and required a 72 h reaction time with 35 mM of aglycon (4). This procedure provided a white flocculent solid (7.7 mg, 14%). The diagnostic glucose H-1 $^1H$ signal was readily identified by characterization of the product by TOCSY with an 800 MHz spectrometer at 45° C. and comparing the resulting spectrum with that of the 2'-N-acyldecanoyl-glucosyl vancomycin neoglycoside. The value of $J_{1,2}$ was obtained from the 1D $^1H$ spectrum at 45° C. with an 800 MHz spectrometer. Diagnostic $^1H$ NMR peak (800 MHz, DMSO-$d_6$, 318 K): δ 4.05 (d, $J_{1,2}$=8.8 Hz, glucose H-1). FT-MALDI-MS m/z calculated for $C_{72}H_{88}Cl_2N_{10}O_{23}$ [M+Na$^+$] 1553.5, observed 1553.5.

4'-N-acyldecanoyl-glucosyl vancomycin neoglycoside (17). Compound (17) was prepared according to the procedure described above and required a 24 h reaction time with 43 mM of aglycon (4). This procedure provided a white flocculent solid (12 mg, 26%). The diagnostic glucose H-1 $^1H$ signal was readily identified by characterization of the product by TOCSY with an 800 MHz spectrometer at 45° C. and comparing the resulting spectrum with that of the 2'-N-acyldecanoyl-glucosyl vancomycin neoglycoside. The value of $J_{1,2}$ was obtained from the 1D $^1H$ spectrum at 45° C. with an 800 MHz spectrometer. Diagnostic $^1H$ NMR peak (800 MHz, DMSO-$d_6$, 318 K): δ 3.99 (d, $J_{1,2}$=8.8 Hz, glucose H-1). FT-MALDI-MS m/z calculated for $C_{72}H_{88}Cl_2N_{10}O_{23}$ [M+Na]$^+$ 1553.5, observed 1553.6.

6'-N-acyldecanoyl-glucosyl vancomycin neoglycoside (18). Compound (18) was prepared according to the procedure described above and required a 72 h reaction time with 25 mM of aglycon (4). A white flocculent solid (11 mg, 14%) was produced. Analysis by TOCSY with a 500 MHz spectrometer at 77° C. showed two sets of spin systems that were most prominent in the glycolipid regions of the spectrum. Two anomeric signals (4.29 and 4.03 ppm) were identified by additional HSQC analysis, both having coupling constants consistent with a β anomeric configuration. This compound exists in two conformational isomers (probably cis and trans amide isomers) that interconvert slowly on the NMR time scale. Diagnostic $^1H$ NMR peaks (500 MHz, DMSO-$d_6$, 350 K): δ 4.03 (d, $J_{1,2}$=9.0 Hz, glucose H-1), 4.29 (d, $J_{1,2}$=8.0 Hz, glucose H-1). FT-MALDI-MS m/z calculated for $C_{72}H_{88}Cl_2N_{10}O_{23}$ [M+Na]$^+$ 1553.5, observed 1553.5.

2'-N-acylbiphenyl-glucosyl vancomycin neoglycoside (19). The product was prepared according to the procedure described above and required a 46 h reaction time with 130 mM of aglycon (4). A white flocculent solid (20 mg, 15%) was produced. The diagnostic glucose H-1 $^1H$ signal was readily identified by characterization of the product by TOCSY with a 500 MHz spectrometer at 60° C. and comparison of the resulting spectrum with that of the 2'-N-acyldecanoyl-glucosyl vancomycin neoglycoside. Diagnostic $^1H$ NMR peak (500 MHz, DMSO-$d_6$, 318 K): δ 4.24 (d, $J_{1,2}$=10.0 Hz, glucose H-1). FT-MALDI-MS m/z calculated for $C_{76}H_{80}Cl_2N_{10}O_{23}$ [M+Na]$^+$ 1593.5, observed 1593.5.

3'-N-acylbiphenoyl-glucosyl vancomycin neoglycoside (20). The product was prepared according to the procedure described above and required a 24 h reaction time with 60 mM of aglycon (4). A white flocculent solid (6.1 mg, 15%) was produced. The diagnostic glucose H-1 $^1H$ signal was readily identified by characterization of the product by TOCSY with an 800 MHz spectrometer at 45° C. and comparison of the resulting spectrum with that of the 2'-N-acyldecanoyl-glucosyl vancomycin neoglycoside. The value of $J_{1,2}$ was obtained from the 1D 1H spectrum at 45° C. with an 800 MHz spectrometer. Diagnostic $^1H$ NMR peak (800 MHz, DMSO-$d_6$, 318 K): δ 4.08 (d, $J_{1,2}$=8.8 Hz, glucose H-1). FT-MALDI-MS m/z calculated for $C_{76}H_{80}Cl_2N_{10}O_{23}$ [M+Na]$^+$ 1593.5, observed 1593.6.

4'-N-acylbiphenoyl-glucosyl vancomycin neoglycoside (21). Compound (21) was prepared according to the procedure described above and required a 39 h reaction time with 80 mM of aglycon (4). A white flocculent solid (13 mg, 26%) was produced. The diagnostic glucose H-1 $^1H$ signal was readily identified by characterization of the product by TOCSY with an 800 MHz spectrometer at 45° C. and comparison of the resulting spectrum with that of the 2'-N-acyldecanoyl-glucosyl vancomycin neoglycoside. The value of $J_{1,2}$ was obtained from the 1D 1H spectrum at 45° C. with an 800 MHz spectrometer. Diagnostic $^1H$ NMR peak (800 MHz, DMSO-$d_6$, 318 K): δ 4.02 (d, $J_{1,2}$=8.8 Hz, glucose H-1). FT-MALDI-MS m/z calculated for $C_{76}H_{80}Cl_2N_{10}O_{23}$ [M+Na]$^+$ 1593.5, observed 1593.9.

6'-N-acylbiphenoyl-glucosyl vancomycin neoglycoside (22). Compound (22) was prepared according to the procedure described above and required a 24 h reaction time with 29 mM of aglycon (4). A white flocculent solid (19 mg, 30%) was produced. The diagnostic glucose H-1 $^1H$ signal was readily identified by characterization of the product by TOCSY with an 800 MHz spectrometer at 45° C. and comparison of the resulting spectrum with that of the 2'-N-acyldecanoyl-glucosyl vancomycin neoglycoside. The value of $J_{1,2}$ was obtained from the 1D 1H spectrum at 45° C. with an 800 MHz spectrometer. Diagnostic $^1H$ NMR peak (800 MHz, DMSO-d$_6$, 318 K): δ 4.01 (d, J$_{1,2}$=8.8 Hz, glucose H-1). FT-MALDI-MS m/z calculated for C$_{76}$H$_{80}$Cl$_2$N$_{10}$O$_{23}$ [M+Na]$^+$ 1593.5, observed 1593.6.

Synthesis Of Aminoglucosides

Figure 4:
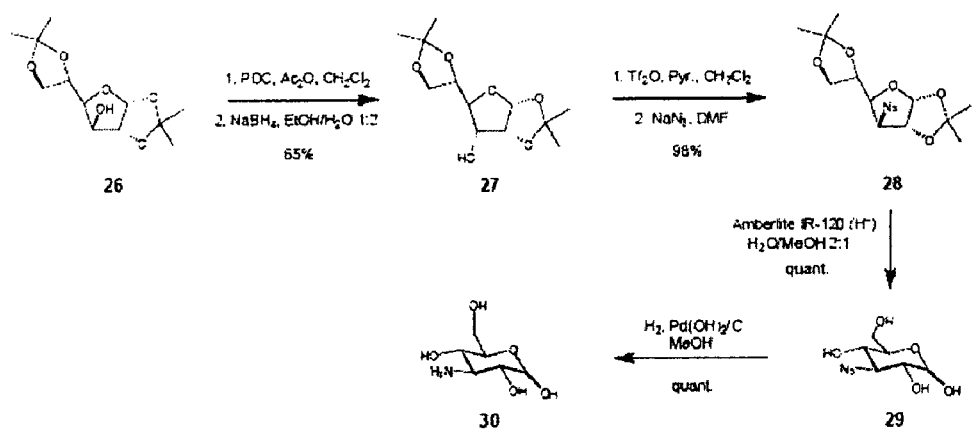
FIG. 4: Synthesis of 3-amino-D-glucopyranose (30).

Referring now to FIG. 4, the synthesis of aminoglucosides can be seen. 1,2:5,6-Di-O-isopropylidene-α-D-allofuranose (27) was prepared according to literature procedure, and spectral data were consistent with the results reported therein.[16]

3-Azido-1,2:5,6-di-O-isopropylidene-α-D-glucofuranose (28) was prepared according to a modified literature procedure.[17,18] To a solution of 1,2:5,6-Di-O-isopropylidene-α-D-allofuranose (25 g, 96 mmol) in pyridine (30 mL) and CH$_2$Cl$_2$ (380 mL) at −10° C., triflic anhydride (19 mL, 33 g, 120 mmol) was slowly added. After 1 h, the reaction mixture was diluted with CH$_2$Cl$_2$ (300 mL). The organic layer was washed with 1 N HCl (300 mL), saturated NaHCO$_3$ (300 mL), and brine (300 mL) and dried over Na$_2$SO$_4$. The solvent was removed under reduced pressure and co-evaporated with toluene. The residue was dissolved in DMF (150 mL), and NaN$_3$ (19 g, 290 mmol) was added. The mixture was stirred for 18 h at rt. The solvent was removed under reduced pressure, and the residue was partitioned between H$_2$O (200 mL) and CH$_2$Cl$_2$ (200 mL). The aqueous layer was extracted with two portions of CH$_2$Cl$_2$ (200 mL), and the combined organic layers were dried over Na$_2$SO$_4$ and concentrated under reduced pressure. The residue was purified by FCC (10% EtOAc in petroleum ether) to provide the desired product (27 g, 98%). Spectral data were consistent with the results reported in the literature.[17]

3-Azido-D-glucopyranose (29) was prepared according to a modified literature procedure.[19] To a solution of 3-Azido-1,2:5,6-di-O-isopropylidene-α-D-glucofuranose (2.7 g, 9.5 mmol) in MeOH/H$_2$O 1:2 (120 mL) was added Amberlite IR-120 acidic resin (26 g), and the mixture was stirred at 40° C. for 19 h. The resin was filtered away, and the solvent was removed under reduced pressure to furnish the desired product (1.9 g, 100%). $^1$H NMR (D$_2$O, 400 MHz): δ 5.17 (d, 1H), 4.65 (d, 1H), 3.86-3.62 (m, 7H), 3.53-3.39 (m, 4H), 3.21 (m, 1H). $^{13}$C NMR (D$_2$O, 100 MHz): δ 96.2, 91.8, 76.8, 73.1, 71.5, 70.6, 68.9, 68.8, 68.7, 66.2, 60.8, 60.6.

3-Amino-D-glucopyranose (30). Palladium hydroxide on charcoal (20%, 0.10 g) was added to a solution of 3-azido-D-glucopyranose (3.47 g, 16 mmol) in MeOH (100 mL). Hydrogen bubbles were passed through the mixture for 1 h. The mixture was then filtered through a pad of Celite™, and the filtrate was concentrated under reduced pressure to provide the product as a colorless foam (2.9 g, 100%). Spectral data were consistent with the results reported in the literature.[20]

Figure 5:
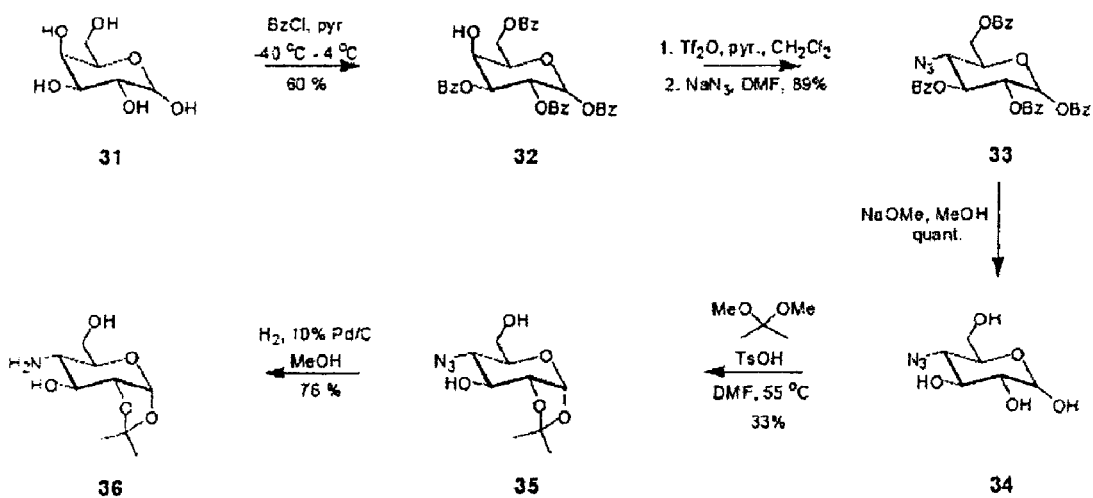
FIG. 5: Synthesis of 4-amino-1,2-o-isopropylidene-α-D-glucopyranose (36).

Referring now to FIG. 5, synthesis of 1,2,3,6-tetra-O-benzoyl-D-galactopyranose (31) can be seen. 1,2,3,6-tetra-O-benzoyl-D-galactopyranose (31) was prepared according to a modification of the literature procedure for preparing the corresponding methyl glycoside.[7] $^1$H NMR (CDCl$_3$, 400 MHz): δ 8.11-8.01 (m, 4H), 7.95-7.24 (m, 16H), 6.86 (d, 1H), 6.14 (dd, 1H), 5.91 (dd, 1H), 4.74 (dd, 1H), 4.60 (m, 2H), 4.53 (dd, 1H); $^{13}$C NMR (CDCl$_3$, 100 MHz): δ 166.7, 166.2, 165.8, 164.8, 133.9, 133.6, 133.4 (2C), 130.0 (2C), 129.9 (2C), 129.8 (4C), 129.4, 129.3, 129.1, 129.0, 128.8 (2C), 128.6 (2C), 128.5 (4C), 91.0, 71.2, 70.9, 67.7, 67.5, 63.1. ESI-MS: m/z calculated for C$_{34}$H$_{28}$O$_{10}$ [M+H]$^+$ 597.2, observed 597.2.

1,2,3,6-tetra-O-benzoyl-4-O-Tf-D-galactopyranose (32) was prepared according to the procedure used above for preparing 3-azido-1,2:5,6-di-O-isopropylidene-α-D-glucofuranose. $^1$H NMR (CDCl$_3$, 400 MHz): δ 8.08-7.88 (m, 8H), 7.61-7.27 (m, 12H), 6.92 (d, 1H), 6.13 (dd, 1H), 6.00 (dd, 1H), 5.79 (d, 1H), 4.87 (t, 1H), 4.73 (dd, 1H), 4.36 (dd, 1H); $^{13}$C NMR (CDCl$_3$, 100 MHz): δ 165.9, 165.8, 165.3, 164.4, 134.2, 134.1, 133.8, 133.7, 130.3 (2C), 130.0 (3C), 129.9 (3C), 129.8 (3C), 128.9 (2C), 128.7 (4C), 128.6 (2C), 128.5, 128.2, 90.3, 82.0, 68.6, 67.9, 66.8, 61.0. ESI-MS: m/z calculated for C$_{35}$H$_{27}$F$_3$O$_{12}$S [M+H]$^+$ 729.1, observed 729.1.

4-Azido-1,2,3,6-tetra-O-benzoyl-D-glucopyranose (33) was prepared according to the procedure used above for preparing 3-azido-1,2:5,6-di-O-isopropylidene-α-glucofuranose. $^1$H NMR (CDCl$_3$, 400 MHz): δ 8.11-7.87 (m, 8H), 7.62-7.29 (m, 12H), 6.80 (d, 1H), 6.16 (t, 1H), 5.58 (dd, 1H), 4.68 (d, 2H), 4.26 (td, 1H), 4.10 (t, 1H); $^{13}$C NMR (CDCl$_3$, 100 MHz): δ 166.2, 165.8, 165.6, 164.5, 134.1, 133.9, 133.7, 133.6, 130.1 (2C), 130.0 (6C), 129.7, 129.2, 129.0 (2C), 128.9, 128.7 (4C), 128.6 (2C), 128.4, 90.2, 71.3, 71.1, 70.5, 63.0, 60.7. ESI-MS: m/z calculated for C$_{34}$H$_{27}$N$_3$O$_9$ [M+Na]$^+$ 644.3, observed 644.3.

4-Azido-D-glucopyranose (34) was prepared under Zemplén conditions.[22] The reaction was neutralized with Amberlite IR-120 acidic resin and filtered. The filtrate was concentrated under reduced pressure, and the resulting crude material was purified by FCC (10% MeOH/CH$_2$Cl$_2$ to 30% MeOH/CH$_2$Cl$_2$) to give the product as a pale brown glass. $^1$H NMR (CD$_3$OD, 400 MHz): δ 5.14 (d, 1H), 4.46 (d, 1H), 3.81 (t, 1H), 3.81 (dd, 1H), 3.72 (m, 2.0H), 3.69 (m, 1H), 3.69 (dd, 1H), 3.50 (t, 1H), 3.42 (dd, 1H), 3.39 (dd, 1H), 3.39 (dd, 1H), 3.21 (m, 1H), 3.18 (dd, 1H). $^{13}$C NMR (CD$_3$OD, 100 MHz): δ 98.3, 94.1, 77.5, 76.5, 76.3, 74.0, 73.9, 71.4, 63.8, 63.6, 62.7, 62.6. ESI-MS: m/z calculated for C$_6$H$_{11}$N$_3$O$_5$ [M+Na]$^+$ 228.1, observed 228.1.

4-Azido-1,2-O-isopropylidene-α-D-glucopyranose (35). 2,2-dimethoxypropane (3.2 mL, 26 mmol) and p-toluenesulfonic acid (0.25 g, 1.3 mmol) were added to a solution of 4-azido-D-glucopyranose (2.6 g, 13 mmol) in DMF (20 mL) under Ar at rt. The temperature was increased to 55° C., and the reaction was stirred for 45 min., after which time it was quenched by the addition of saturated aq NaHCO$_3$ until the solution was neutral, as judged by pH paper. The volatiles were removed under high vacuum, and the resulting residue was purified by FCC (2.5% MeOH/CH$_2$Cl$_2$ to 30% MeOH/CH$_2$Cl$_2$) to give the desired product (1.0 g, 33%) as a yellow glass. $^1$H NMR (CD$_3$OD, 400 MHz): δ 5.62 (d, 1H), 4.14 (t, 1H), 3.99 (t, 1H), 3.74 (m, 2H), 3.68 (m, 1H), 3.42 (dd, 1H), 1.54 (s, 3H), 1.29 (s, 3H); $^{13}$C NMR (CD$_3$OD, 100 MHz): δ 110.3, 98.7, 77.8, 73.3, 72.7, 63.1, 61.8, 27.4, 26.5. ESI-MS: m/z calculated for C$_9$H$_{15}$N$_3$O$_5$ [M+H]$^+$246.1, observed 246.1.

4-Amino-1,2-O-isopropylidene-D-glucopyranose (36). Palladium hydroxide on charcoal (10%, 0.10 g) was added to a solution of 4-azido-1,2-O-isopropylidene-D-glucopyranose (0.80 g, 3.3 mmol) in MeOH (30 mL). Hydrogen bubbles were passed through the mixture for 1 h. The mixture was then filtered through a pad of diatomaceous earth, and the filtrate was concentrated under reduced pressure to give a pale yellow solid (0.55 g, 76%) as product. $^1$H NMR (CD$_3$OD, 400 MHz): δ 5.61 (d, 1H), 4.14 (t, 1H), 3.81 (t, 1H), 3.77 (dd, 1H), 3.72 (dd, 1H), 3.63 (m, 1H), 2.74 (dd, 1H), 1.56 (s, 3H), 1.38 (s, 3H); $^{13}$C NMR (CD$_3$OD, 100 MHz): δ 110.3, 98.7, 77.9, 76.0, 74.1, 63.9, 53.0, 27.3, 26.3. ESI-MS: m/z calculated for C$_9$H$_{17}$NO$_5$ [M−H]$^-$ 218.0, observed 218.0.

Figure 6:
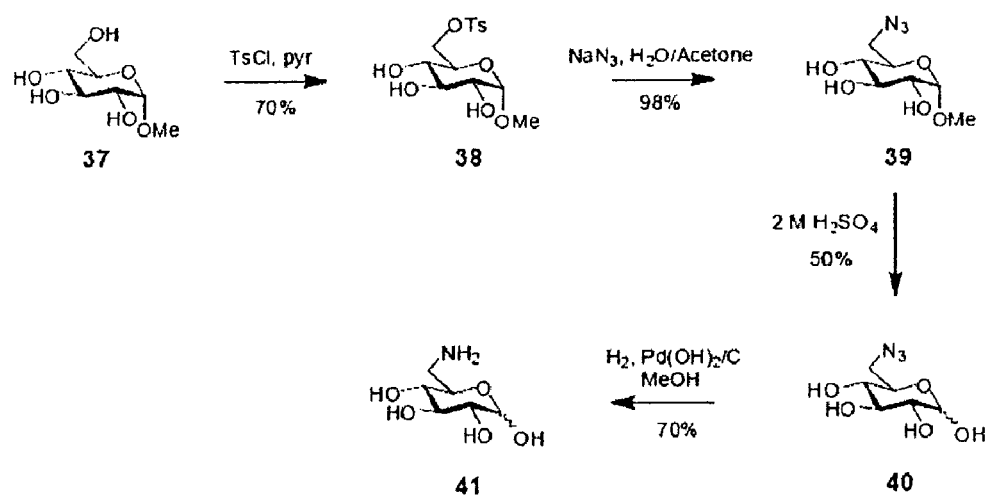
FIG. 6: Synthesis of 6-amino-D-glucopyranose (41).

Referring now to FIG. 6, synthesis of 6-Tosyl-methyl-α-D-OMe-glucopyranoside (38) can be seen. 6-Tosyl-methyl-α-D-OMe-glucopyranoside (38) was prepared according to the literature procedure for preparing the corresponding mannoside.[23] Spectral data were consistent with the results reported in the literature.[24,25]

6-Azido-methyl-α-D-OMe-glucopyranoside (39) was prepared according to the literature procedure for preparing the corresponding mannoside.[23] Spectral data were consistent with the results reported in the literature.[26]

6-Azido-D-glucopyranose (40) was prepared according to the literature procedure for preparing the corresponding mannoside[23]. Spectral data were consistent with the results reported in the literature.[27]

6-Amino-D-glucopyranose (41) was prepared according to the literature procedure for preparing the corresponding mannoside[23]. Spectral data were consistent with the results reported in the literature.[28]

Synthesis of Lipoglucosides

Figure 7:
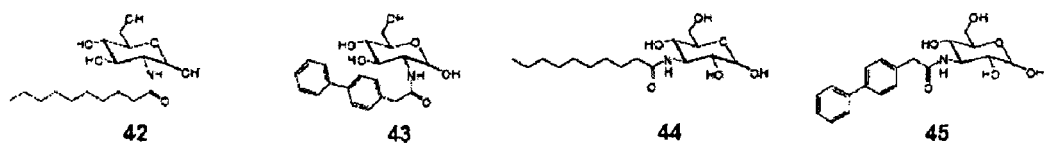
FIG. 7: 2- and 3-N-acyl gyucopyranoses.

Referring to FIG. 7, the 2-N-acyldecanoyl-D-glucose (42) compound is now described. 2-N-acyldecanoyl-D-glucose (42) was prepared according to literature procedure for the preparation of a slightly different lipoglucoside.[29] $^1$H NMR (DMSO-$d_6$, 400 MHz): δ 7.62 (d, 0.2H), 7.47 (d, 1.0H), 6.44 (d, 0.2H), 6.36 (d, 1.0H), 4.90 (t, 1.2H), 4.86 (d, 1.0H), 4.75 (d, 0.2H), 4.53 (d, 1.0H), 4.49 (t, 0.2H), 4.42 (d, 0.2H), 4.39 (t, 1.0H), 3.68-3.41 (m, 6.0H), 3.12-3.02 (m, 1.2H), 2.17 (t, 0.4 H), 2.08 (t, 2.0 H), 1.45 (p, 2.4H), 1.23 (m, 14.4H), 0.85 (t, 3.6H). $^{13}$C NMR (DMSO-$d_6$, 100 MHz): δ 172.3, 90.6, 72.0, 71.2, 70.4, 61.1, 54.2, 35.3, 31.3, 28.9 (2C), 28.8, 28.7, 25.3, 22.1, 14.0. ESI-MS: m/z calculated for $C_{16}H_{31}NO_6$ [M+H]$^+$ 334.2, observed 334.3.

2-N-acylbiphenoyl-D-glucose (43). Glucosamine hydrochloride (2.2 g, 10 mmol) and Et$_3$N (2.2 mL, 16 mmol) were added to a solution of 4-biphenylacetic acid succinimide ester (1.5 g, 4.9 mmol) in DMF (15 mL), and the mixture was stirred at rt under Ar for 36 h. The volatiles were removed under high vacuum, and the resulting residue was purified via FCC (5% MeOH/CH$_2$Cl$_2$ to 50% MeOH/CH$_2$Cl$_2$) to give the desired product mixed with residual impurities. This material was dispersed in boiling MeOH (40 mL), and the solution was allowed to cool to rt, at which time it was filtered through glass wool. The retentate was washed with rt MeOH (3×3 mL) and recovered with boiling MeOH. The solvent was removed under reduced pressure, and the material was stored under high vacuum to yield the desired product as a white solid (1.1 g, 61%) as a white solid. $^1$H NMR (DMSO-$d_6$, 400 MHz): δ 7.62 (d, J=7.6 Hz, 2H), 7.55 (d, J=8.4 Hz, 2H), 7.43 (t, J=7.6 Hz, 2H), 7.36 (d, J=8.4 Hz, 2H), 7.32 (t, J=7.2 Hz, 1H), 4.95 (d, J=3.2 Hz, 1H), 3.62 (m, 1H), 3.61 (m, 2H), 3.56 (m, 1H), 3.52 (m, 2H), 3.48 (m, 1H), 3.15 (t, J=8.8 Hz, 1H). $^{13}$C NMR (DMSO-$d_6$, 400 MHz): δ 170.67, 140.43, 138.57, 136.14, 129.96 (2C), 129.11 (2C), 127.44, 126.77 (2C), 126.66 (2C), 90.84, 72.29, 71.33, 70.71, 61.31, 54.64, 41.95. ESI-MS: m/z calculated for $C_{20}H_{23}NO_6$ [M+H]$^+$.374.15, observed 374.2. HRMS: m/z calculated for $C_{20}H_{23}NO_6$ [M+Na]$^+$ 396.1423, observed 396.1419.

3-N-acyldecanoyl-D-glucose (44). 3-N-acyldecanoyl-D-glucose (44) was prepared according to procedure used for 2-N-acylbiphenoyl-D-glucose except for purification, which was accomplished by FCC (11% MeOH/CH$_2$Cl$_2$, then 20% MeOH/CH$_2$Cl$_2$) to provide the desired product (1.95 g, 36%). $^1$H NMR (CD$_3$OD, 400 MHz): δ 5.09 (d, 1.0H), 4.52 (d, 1.0H), 4.09 (t, 1.0H), 3.84-3.61 (m, 6.0H), 3.42-3.29 (m, 4.0 H), 3.16 (dd, 1.0H), 2.24 (t, 4.0H), 1.61 (m, 4.0H), 1.28 (m, 24H), 0.88 (m, 6.0H). $^{13}$C NMR (CD$_3$OD, 100 MHz): δ 178.0, 177.8, 98.9, 93.4, 79.3, 74.4, 73.4, 72.2, 70.4, 70.3, 62.8, 62.6, 59.1 (2C), 55.7 (2C), 37.5 (2C), 37.4, 33.0 (2C), 30.6, 30.5, 30.4, 30.3, 27.0 (2C), 26.9, 23.7 (2C), 14.4 (2C). ESI-MS: m/z calculated for $C_{16}H_{31}NO_6$ [M+H]$^+$ 334.2, observed 334.2. HRMS: m/z calculated for $C_{16}H_{31}NO_6$ [M+Na]$^+$ 356.2049, observed 356.2066.

3-N-acylbiphenoyl-D-glucose (45). 3-N-acylbiphenoyl-D-glucose (45) was prepared according to the procedure used for 2-N-acylbiphenoyl-D-glucose, and the crude residue was purified by FCC (2.5% MeOH/CH$_2$Cl$_2$ to 40% MeOH/CH$_2$Cl$_2$) to give the desired product (67 mg, 18%). $^1$H NMR (DMSO-$d_6$, 400 MHz): δ 7.46 (m, 8H), 7.34 (m, 8H), 7.22 (t, J=7.2 Hz, 12), 5.09 (d, J=3.6 Hz, 1H), 4.52 (d, J=7.6 Hz, 1H), 4.12 (t, J=10 Hz, 1H), 3.81 (dd, J=2.4, 11.2 Hz, 1H), 3.80 (m, 2H), 3.74 (dd, J=2.4, 11.2 Hz, 1H), 3.66 (dd, J=5.2, 11.2 Hz, 1H), 3.62 (dd, J=5.2, 11.2 Hz, 1H), 3.57 (s, 4H), 3.45 (dd, J=3.6, 10.4 Hz, 1H), 3.39 (t, J=10 Hz, 1H), 3.37 (t, J=9.6 Hz, 1H), 3.33 (d, J=2.2, 5.2 Hz, 1H), 3.22 (dd, J=7.6, 10 Hz, 1H). $^{13}$C NMR (DMSO-$d_6$, 100 MHz): δ 175.64, 175.44, 142.17, 140.96, 136.21, 136.19, 130.89 (2C), 130.87 (2C), 129.92 (4C), 128.33, 128.33, 128.10 (4C), 127.92 (4C), 127.65, 126.96, 99.05, 93.59, 79.40, 74.51, 73.59, 72.22, 70.39, 70.25, 62.87, 62.74, 59.50, 56.05, 43.78, 43.71. ESI-MS: m/z calculated for $C_{20}H_{23}NO_6$ [M+H]$^+$ 374.15, observed 374.2. HRMS: m/z calculated for $C_{20}H_{23}NO_6$ [M+H]$^+$ 374.1604, observed 374.1605.

Figure 8:
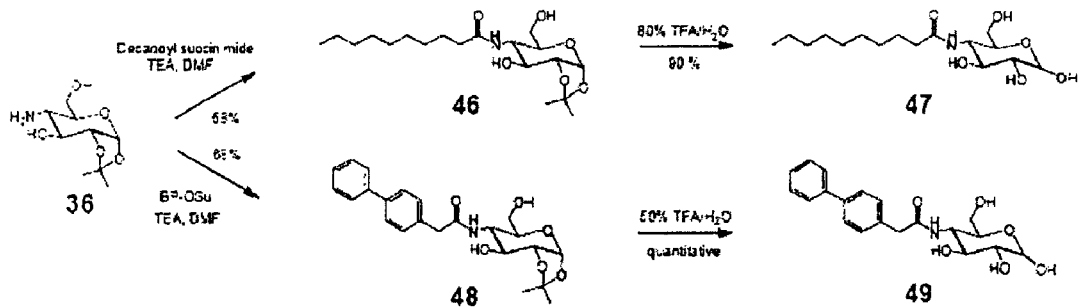
FIG. 8: Synthesis of 4-N-decanoyl-D-gucose (48) and 4-N-biphenoyl-D-glucose (49).

Referring now to FIG. 8, the synthesis of 4-N-acyldecanoyl-1,2-O-isopropylidene-glucopyranose (46) can be seen. 4-N-acyldecanoyl-1,2-O-isopropylidene-glucopyranose (46) was prepared according to the procedure described above for 2-N-acyldecanoyl-D-glucose except for purification, which was accomplished by FCC (1% MeOH/CH$_3$Cl to 10% MeOH/CH$_3$Cl) to give the desired product (120 mg, 58%). $^1$H NMR (CD$_3$OD, 400 MHz): δ 5.67 (d, 1H), 4.25 (t, 1H), 4.12 (t, 1H), 3.99 (t, 1H), 3.71 (m, 2H), 3.66 (m, 1H), 2.19 (t, 2H), 1.60 (m, 2H), 1.58 (s, 3H), 1.37 (s, 3H), 1.26 (m, 12H), 0.88 (t, 3H); $^{13}$C NMR (CD$_3$OD, 100 MHz): δ 174.1, 109.4, 96.8, 74.8, 72.7, 69.7, 62.8, 49.0, 36.6, 31.9, 29.5, 29.4, 29.3, 29.2, 26.5, 25.7, 25.6, 22.7, 14.1. ESI-MS: m/z calculated for $C_{19}H_{35}NO_6$ [M−H]$^-$ 372.2, observed 372.2. HRMS: m/z calculated for $C_{19}H_{35}NO_6$ [M+H]$^+$ 373.2464, observed 373.2451.

4-N-decanoyl-D-glucose (47). 4-N-acyldecanoyl-1,2-O-isopropylidene-D-glucopyranose (140 mg, 0.38 mmol) was hydrolyzed in 80% TFA in H$_2$O (3.4 ml) at room temperature for 1 h. The mixture was evaporated under reduced pressure and azeotroped with MeOH (2×10 ml) to give 4-N-acyldecanoyl-D-glucose (112 mg, 90%) as a white powder. $^1$H NMR (CD$_3$OD, 400 MHz): δ 5.23 (d, J=3.6 Hz, 1H), 4.56 (d, J=3.6 Hz, 1H), 3.79 (m, 4H), 3.59 (m, 5H), 3.53 (m, 1H), 3.51 (m, 1H), 3.25 (t, J=7.6 Hz, 1H), 2.29 (t, J=7.6 Hz, 4H), 1.64 (m, 4H), 1.26 (m, 24H), 0.92 (t, J=6.8 Hz, 6H). $^{13}$C NMR (CD$_3$OD, 100 MHz): δ 178.0, 178.0, 97.8, 93.8, 77.0, 76.7, 75.0, 74.1, 72.2, 71.8, 62.8, 62.8, 53.1, 53.1, 37.3 (2C), 32.9 (2C), 30.5 (2C), 30.4 (2C), 30.3 (2C), 30.3 (2C), 27.0, 23.7 (2C), 14.6 (2C). ESI-MS: m/z calculated for $C_{16}H_{31}NO_6$ [M−H]$^-$ 332.2, observed 332.2.

4-N-acylbiphenoyl-1,2-O-isopropylidene-D-glucopyranose (48). 4-Amino-1,2-O-isopropylidene-D-glucopyranose (45 mg, 0.21 mmol) was dissolved in DMF (1 mL) at rt under Ar. To this solution was added biphenylacetic acid succinimide ester (BP-OSu, 71 mg, 0.23 mmol) and Et$_3$N (58 uL, 0.42 mmol), and the reaction was stirred overnight at rt. The volatiles were removed under reduced pressure, and the crude residue was purified by FCC (5% MeOH/CH$_2$Cl$_2$ to 20% MeOH/CH$_2$Cl$_2$) to give the product (37 mg, 68%). $^1$H NMR (CD$_3$OD, 400 MHz): δ 7.60-7.57 (m, 4H), 7.43-7.32 (m, 5H), 5.56 (d, 1H), 4.16-4.13 (m 1H), 3.89-3.88 (m 2H), 3.67-3.63 (m, 1H), 3.61-3.55 (m, 4H), 1.42 (s, 3H), 1.30 (s, 3H); $^{13}$C NMR (CD$_3$OD, 100 MHz): δ 174.1, 142.1, 141.5, 135.8, 131.0 (2C), 130.0 (2C), 128.5 (3C), 128.0 (2C), 100.6, 98.3, 77.0, 73.6, 71.5, 63.9, 51.2, 43.6, 26.9, 26.0. ESI-MS: m/z calculated for $C_{23}H_{27}NO_6$ [M−H]⁻ 412.1, observed 412.1. HRMS: m/z calculated for $C_{23}H_{27}NO_6$ [M+Na]⁺ 849.3574, observed 849.3569.

4-N-biphenoyl-D-glucose (49). 4-N-acylbiphenoyl-1,2-O-isopropylidene-D-glucopyranose (37 mg, 0.14 mmol) was dissolved in TFA/H₂O (1:1, 1 mL), and the solution was stirred at rt for 1 h. The volatiles were removed under reduced pressure, and the material was azeotroped three times with MeOH (10 mL) and stored under high vacuum overnight to give the desired product (33 mg, quantitative). ¹H NMR (CD₃OD, 400 MHz): δ 7.60-7.55 (m 8H), 7.43-7.38 (m 8H), 7.33-7.29 (m 2H), 5.13 (d, 1H), 4.45 (d, 1H), 3.84-3.79 (m, 2H), 3.73-3.64 (m, 4H), 3.59 (s, 2H), 3.52-3.39 (m, 5H), 3.34 (s, 2H), 3.18 (dd, 1H); ¹³C NMR (CD₃OD, 100 MHz): δ 175.1, 174.9, 142.0, 141.1, 135.7 (2C), 130.5 (4C), 130.0 (4C), 128.2 (4C), 128.1 (4C), 127.8 (4C), 98.1, 93.9, 77.1, 76.9, 75.1, 74.4, 72.1, 71.9, 63.0 (2C), 53.3, 53.2, 43.6, 43.5. ESI-MS: m/z calculated for $C_{20}H_{23}NO_6$ [M+H]+374.1, observed 374.1. HRMS: m/z calculated for $C_{20}H_{23}NO_6$ [M+Na]⁺ 396.1423, observed 396.1426.

Figure 9:
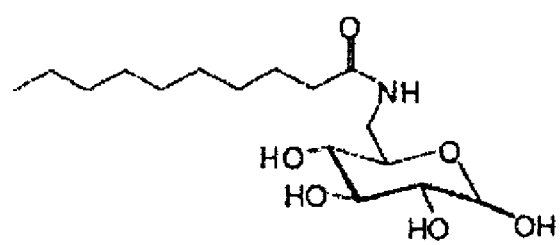
FIG. 9: 6-N-acyl glucopyranoses.
Figure 9:
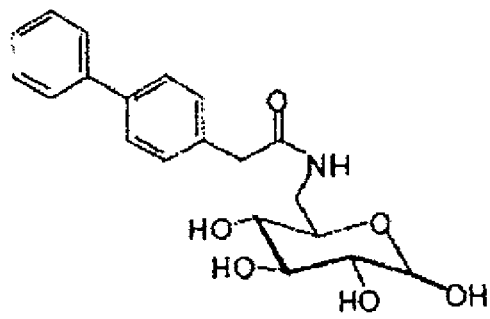

Referring now to FIG. 9, 6-N-acyldecanoyl-D-glucose (50) is shown. 6-N-acyldecanoyl-D-glucose (50) was prepared according to the procedure used for 2-N-acyldecanoyl-D-glucose except for purification, which was accomplished by FCC (20% MeOH/CHCl₃) to furnish the desired product (2.2 g, 49%). ¹H NMR (DMSO-d₆, 400 MHz): δ 7.86 (t, 1H), 7.74 (t, 1H), 6.60 (d, 1H), 6.22 (d, 1H), 4.99 (d, 1H), 4.92-4.88 (m, 2H), 4.74 (b, 1H), 4.55 (b, 1H), 4.25 (d, 1H), 3.59-3.55 (m, 1H), 3.48-3.33 (m, 2H), 3.16-3.08 (m, 3H), 2.90-2.82 (m, 4H), 2.06 (t, 4H), 1.47-1.44 (m, 4H), 1.23 (s, 24H), 0.84 (t, 6H); ¹³C NMR (DMSO-d₆, 100 MHz): δ 172.9, 172.8, 97.0, 92.2, 76.0, 74.9, 74.5, 72.5, 72.4, 71.9, 71.6, 69.1, 45.3 (2C), 40.3 (2C), 35.2 (2C), 31.3 (2C), 28.9, 28.8, 28.7, 25.3 (2C), 25.2 (2C), 22.1 (2C), 14.0 (2C), 8.5. ESI-MS: m/z calculated for $C_{16}H_{31}NO_6$ [M+Na]⁺ 356.2, observed 356.2. HRMS: m/z calculated for $C_{16}H_{31}NO_6$ [M+Na]⁺ 356.2049, observed 356.2039.

6-N-acylbiphenoyl-D-glucose (51). 6-N-acylbiphenoyl-D-glucose (51) was prepared according to the procedure used for 2-N-acyldecanoyl-D-glucose except for purification, which was accomplished by FCC (5% MeOH/CH₂Cl₂ to 30% MeOH/CH₃Cl) to give the desired product (130 mg, 94%). ¹H NMR (DMSO-d₆, 400 MHz): δ 7.64 (m, 4H), 7.59 (d, J=8.4 Hz, 4H), 7.45 (t, J=7.6 Hz, 4H), 7.39 (d, J=8.4 Hz, 4H), 7.34 (t, J=7.6 Hz, 2H), 5.04 (d, J=3.6 Hz, 1H), 4.41 (d, J=8.0 Hz, 1H), 3.75 (m, J=3.0, 6.4 Hz, 1H), 3.56 (dd, J=3.0, 14 Hz, 1H), 3.55 (s, 4H), 3.55 (t, J=9.6 Hz, 1H), 3.50 (dd, J=3.0, 14 Hz, 1H), 3.36 (dd, J=6.4, 14 Hz, 1H), 3.34 (m, J=6.4, 14 Hz, 1H), 3.28 (m, 1H), 3.25 (t, J=9.0 Hz, 1H), 3.24 (m, J=3.6, 9.6 Hz, 1H), 3.05 (t, J=9.0 Hz, 1H), 3.04 (t, J=9.6 Hz, 1H), 3.04 (m, 1H). ¹³C NMR (DMSO-d₆, 100 MHz): δ 173.51 (2C), 141.96 (2C), 140.58 (2C), 136.89 (2C), 131.09 (4C), 130.30 (4C), 128.69 (2C), 128.19 (4C), 128.10 (4C), 98.22, 94.03, 77.78, 76.31, 76.06, 74.37, 74.01, 73.37, 73.15, 71.54, 43.38 (2C), 41.90, 41.89. ESI-MS: m/z calculated for $C_{20}H_{23}NO_6$ [M+H]⁺ 374.15, observed 374.2. HRMS: m/z calculated for $C_{20}H_{23}NO_6$ [M+Na]⁺ 396.1423, observed 396.1427.

Biological Testing Against VRE

Vancomycin (1), aglycon (4) and liponeoglycopeptides 15-22 were dissolved to a final concentration of 5 mg/mL in 75% DMSO/H₂O. Minimum inhibitory concentrations (MICs, in μg/mL) were determined for each compound against 15 strains of VRE, including well-characterized commercially available strains and clinical isolates. These experiments were performed in Mueller-Hinton broth in a microdilution plate format, according to NCCLS guidelines: *Methods for Dilution Antimicrobial Susceptibility Tests for Bacteria that Grow Aerobically* (approved standard, NCCLS Document M7-A4, National Committee for Clinical Laboratory Standards, Wayne, Pa., ed. 4, 1997).

Those skilled in the art will recognize, or be able to ascertain using no more then routine experimentation, numerous equivalents to the specific compounds, protocols, methods, assays and reagents described herein. Such equivalents are considered to be within the scope of this invention and covered by the following claims. All publications, patents, and patent applications cited herein are hereby incorporated by reference in their entirety for all purposes.

REFERENCES (1) Murray, B. E. *N. Engl. J. Med.* 2000, 342, 710-721.
(2) Kahne, D. et al. *Chem. Rev.* 2005, 705, 425-448.
(3) Weigel, L. M. et al. *Science* 2003, 302, 1569-1571.
(4) Chang, S. et al. S. K. *N. Engl. J. Med.* 2003, 348, 1342-1347.
(5) Nicolaou, K. C. et al. *Chem.-Eur. J.* 2001, 7, 3798-3823.
(6) Dong, S. D. et al. *J. Am. Chem. Soc.* 2002, 724, 9064-9065.
(7) Peri, F.; Dumy, P.; Mutter, M. *Tetrahedron* 1998, 54, 12269-12278.
(8) Peri, F. et al. *Chem. Comm.* 2002, 1504-1505.
(9) Peri, F.; et al. *Chem.-Eur. J.* 2004, 70, 1433-1444.
(10) Langenhan, J. et al. *Proc. Natl. Acad. Sci. U.S.A.* 2005, 702, 12305-12310.
(11) Thompson, C et al. *J. Am. Chem. Soc.* 1999, 727, 1237-1244.
(12) Chen, Z. et al. *Tetrahedron* 2002, 58, 6585-6594.
(13) Nagarajan, R. et al. 1989, 42, 63-72.
(14) Leimkuhler, C. et al. *J. Am. Chem. Soc.* 2005, 727, 3250-3251.
(15) Thompson, C. et al. *J. Am. Chem. Soc.* 1999, 727, 1237-1244.
(16) Pitsch, S. *Helv. Chim. Acta* 1997, 80, 2286-2314.
(17) Sleath, P. R. et al. *J. Org. Chem.* 1991, 56, 3608-3613.
(18) Hall, L. D., Miller, D. C. *Carbohydr. Res.* 1976, 47, 299-305.
(19) Faghih, R. et al. *J. Org. Chem.* 1986, 57, 4558-4564.
(20) Guo, J. T.; Frost, J. W. *J. Am. Chem. Soc.* 2002, 724, 10642-10643.
(21) Williams, J. M., Richardson, A. C. *Tetrahedron* 1967, 23, 1369-1378.
(22) Simple, G. *Beer. Deaths. Chem. Gees.* 1927, 60B, 1555.
(23) Wang, P. et al. *J. Org. Chem.* 1993, 58, 3985-3990.
(24) Dahlhoff, W. V.; Radkowski, K. *Z. Naturforsch.* 1996, 51b, 891-896.
(25) Tsuda, Y. et al. *Chem. Pharm. Bull.* 1991, 39, 2883-2887.
(26) Maunier, V. et al. *Carbohydr. Res.* 1997, 299, 49-57.
(27) Durrwachter, J. R.; Wong, C. H. *J. Org. Chem.* 1988, 53, 4175-4181.
(28) Kadokawa, J. et al. *Chem. Lett.* 1998, 383-384.
(29) Macher, I. *Carbohydr. Res.* 1987, 162, 79-84.

We claim:

1. A method of synthesizing a vancomycin analog from a parent vancomycin compound, comprising the steps of:
   (a) synthesizing an alkoxylamine-containing vancomycin aglycon from the parent vancomycin compound;
   (b) chemoselectively ligating a reducing sugar moiety to the alkoxylamine-containing vancomycin aglycon of step (a) to result in the vancomycin analog; and
   (c) isolating the resulting vancomycin analog of step (b).

2. The method of claim 1, wherein the resulting vancomycin analog is effective in inhibiting growth of Vancomycin Resistant Enterococci (VRE).

3. The method of claim 1, wherein the alkoxylamine-containing vancomycin aglycon is a methoxylamine-containing vancomycin analog.

4. The method of claim 1, wherein the reducing sugar moiety is selected from 2-N-acyldecanoyl-o-glucose, 3-N-acyldecanoyl-o-glucose, 4-N-acyldecanoyl-o-glucose, 6-N-acyldecanoyl-o-glucose, 2-N-acylbiphenoyl-o-glucose, 3-N-acylbiphenoyl-oglucose, 4-N-acylbiphenoyl-o-glucose and 6-N-acylbiphenoyl-o-glucose.

5. The method of claim 1, wherein the vancomycin analog is selected from 2'-N-acyldecanoyl-glucosyl vancomycin neoglycoside, 3'-N-acyldecanoyl-glucosyl vancomycin neoglycoside, 4'-N-acyldecanoyl-glucosyl vancomycin neoglycoside, 6'-N-acyldecanoyl-glucosyl vancomycin neoglycoside, 2'-N-acylbiphenyl-glucosyl vancomycin neoglycoside, 3'-N-acylbiphenoyl-glucosyl vancomycin neoglycoside, 4'-N-acylbiphenoyl-glucosyl vancomycin neoglycoside and 6'-N-acylbiphenoyl-glucosyl vancomycin neoglycoside.

6. The method of claim 1, wherein the reducing sugar moiety stereoselectively ligates to the alkoxylamine containing vancomycin aglycon in a β-position whereby the resulting vancomycin analog is a β-enantiomer.

* * * * *

UNITED STATES PATENT AND TRADEMARK OFFICE
CERTIFICATE OF CORRECTION

| | | |
|---|---|---|
| PATENT NO. | : 8,236,926 B2 | Page 1 of 1 |
| APPLICATION NO. | : 11/850877 | |
| DATED | : August 7, 2012 | |
| INVENTOR(S) | : Jon S. Thorson and Byron R. Griffith | |

It is certified that error appears in the above-identified patent and that said Letters Patent is hereby corrected as shown below:

Col. 1, Lines 14-17 should be replaced with the following: -- This invention was made with government support under AI052218 and CA084374 awarded by the National Institutes of Health. The government has certain rights in the invention. --

Col. 12, Line 9, "-α-glucofur-" should be -- -α-D-glucofura --

Signed and Sealed this
Sixteenth Day of October, 2012

David J. Kappos
*Director of the United States Patent and Trademark Office*